(12) United States Patent
Ueminami et al.

(10) Patent No.: US 9,330,067 B2
(45) Date of Patent: *May 3, 2016

(54) PRINTED NONWOVEN WEB AND METHOD FOR MAKING

(75) Inventors: Atsushi Ueminami, Kobe (JP); David Christopher Oetjen, West Chester, OH (US); Paul Thomas Weisman, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 996 days.

This patent is subject to a terminal disclaimer.

(21) Appl. No.: 13/399,228

(22) Filed: Feb. 17, 2012

(65) Prior Publication Data

US 2012/0150136 A1 Jun. 14, 2012

Related U.S. Application Data

(63) Continuation of application No. 11/710,214, filed on Feb. 23, 2007, now Pat. No. 8,142,876.

(51) Int. Cl.
*B32B 3/24* (2006.01)
*G06F 17/21* (2006.01)
*G06F 17/22* (2006.01)
*G06F 17/30* (2006.01)

(52) U.S. Cl.
CPC .......... *G06F 17/212* (2013.01); *G06F 17/2247* (2013.01); *G06F 17/30905* (2013.01)

(58) Field of Classification Search
CPC .......... D06P 5/00; D06P 5/12; A61F 13/512; A61F 13/8405; D06M 23/16
USPC ............ 428/131, 195.1, 156, 196; 604/385.1, 604/361, 383
See application file for complete search history.

(56) References Cited

U.S. PATENT DOCUMENTS

| 2,881,761 A | 4/1959 | Kenner |
| 3,559,648 A | 2/1971 | Mason, Jr. |
| 3,574,044 A | 4/1971 | Shepherd |
| 4,022,211 A | 5/1977 | Timmons et al. |
| 4,623,340 A | 11/1986 | Luceri |

(Continued)

FOREIGN PATENT DOCUMENTS

| EP | 0 794 280 A2 | 9/1997 |
| EP | 0 934 737 A1 | 8/1999 |

(Continued)

OTHER PUBLICATIONS

PCT International Search Report, mailed Mar. 6, 2008, 5 pages.

(Continued)

*Primary Examiner* — William P Watkins, III
(74) *Attorney, Agent, or Firm* — George H. Leal; Amanda T. Barry

(57) ABSTRACT

A nonwoven web having printed thereon a colorant and/or a composition providing a skin health benefit. The nonwoven web can be a three-dimensional, fluid pervious, polymeric web. The nonwoven web can comprise apertures. The apertures are defined in a first surface of the nonwoven web in a first plane of the nonwoven web, and extend in sidewall portions to a second surface in a second plane of the nonwoven web. A colorant or lotion composition can be deposited on at least a portion of the second surface of the nonwoven web.

20 Claims, 9 Drawing Sheets

(56) References Cited

U.S. PATENT DOCUMENTS

| | | |
|---|---|---|
| 4,662,875 A | 5/1987 | Hirotsu |
| 4,681,576 A | 7/1987 | Colon et al. |
| 4,743,238 A | 5/1988 | Colon et al. |
| 4,895,567 A | 1/1990 | Colon et al. |
| 4,908,026 A | 3/1990 | Sukiennik |
| 4,909,879 A | 3/1990 | Ball |
| 5,006,394 A | 4/1991 | Baird |
| 5,035,691 A | 7/1991 | Zimmel |
| 5,066,711 A | 11/1991 | Colon et al. |
| 5,188,625 A | 2/1993 | Van Iten et al. |
| D340,978 S | 11/1993 | Atcheson et al. |
| 5,261,899 A | 11/1993 | Visscher |
| 5,300,054 A | 4/1994 | Feist |
| 5,304,161 A | 4/1994 | Noel |
| 5,342,861 A | 8/1994 | Raykovitz |
| H1376 H | 11/1994 | Osborn et al. |
| H001376 H | 11/1994 | Osborn, III et al. |
| 5,401,267 A | 3/1995 | Couture-Dorschner |
| 5,437,653 A | 8/1995 | Gilman |
| 5,439,458 A | 8/1995 | Noel |
| 5,454,800 A | 10/1995 | Hirt |
| 5,458,590 A | 10/1995 | Schleinz |
| 5,503,076 A | 4/1996 | Yeo |
| 5,562,037 A | 10/1996 | Schleinz |
| 5,566,616 A | 10/1996 | Schleinz |
| 5,675,079 A | 10/1997 | Gilman et al. |
| 5,683,752 A | 11/1997 | Popp |
| 5,766,389 A | 6/1998 | Brandon |
| 5,818,719 A | 10/1998 | Brandon |
| 5,897,541 A | 4/1999 | Uitenbroek |
| D412,574 S | 8/1999 | Trombetta et al. |
| D423,098 S | 4/2000 | Stancyk, Jr. |
| 6,051,036 A | 4/2000 | Kusaki et al. |
| 6,075,178 A | 6/2000 | LaWilhelm |
| 6,264,640 B1 | 7/2001 | Sutton |
| 6,297,424 B1 | 10/2001 | Olson |
| 6,307,119 B1 | 10/2001 | Cammarota et al. |
| 6,352,563 B1 | 3/2002 | Kusaki et al. |
| 6,353,149 B1 | 3/2002 | Stone |
| 6,506,456 B1 | 1/2003 | Sharma et al. |
| 6,568,530 B2 | 5/2003 | Takahashi et al. |
| 6,595,042 B2 | 7/2003 | Holliday et al. |
| 6,596,918 B1 | 7/2003 | Wehrle et al. |
| 6,601,705 B2 | 8/2003 | Molina et al. |
| 6,617,488 B1 | 9/2003 | Springer et al. |
| 6,651,551 B1 | 11/2003 | Castellanos |
| 6,676,736 B2 | 1/2004 | Nakano et al. |
| 6,681,934 B2 | 1/2004 | Kolterjohn et al. |
| 6,710,221 B1 | 3/2004 | Pierce et al. |
| 6,719,742 B1 | 4/2004 | McCormack et al. |
| 6,732,778 B1 | 5/2004 | Machida et al. |
| 6,733,483 B2 | 5/2004 | Raufman et al. |
| 6,763,944 B2 | 7/2004 | Ronn et al. |
| 6,772,708 B2 | 8/2004 | Klofta et al. |
| 6,904,865 B2 | 6/2005 | Klofta et al. |
| 6,911,573 B2 | 6/2005 | Chen et al. |
| 6,923,321 B2 | 8/2005 | Samolinski et al. |
| 6,926,950 B2 | 8/2005 | Fernfors et al. |
| 6,932,798 B2 | 8/2005 | Kudo et al. |
| 6,936,648 B2 | 8/2005 | Bagwell et al. |
| 6,946,585 B2 | 9/2005 | London Brown |
| 6,949,689 B2 | 9/2005 | Noda et al. |
| 7,041,160 B2 | 5/2006 | Feldkamp |
| 7,159,532 B2 | 1/2007 | Klofta et al. |
| 7,163,528 B2 | 1/2007 | Christon et al. |
| 7,189,888 B2 | 3/2007 | Wang et al. |
| 7,198,742 B2 | 4/2007 | Gerndt |
| 7,270,651 B2 | 9/2007 | Christon et al. |
| 7,306,582 B2 | 12/2007 | Christon et al. |
| 7,537,585 B2 | 5/2009 | Christon et al. |
| 7,736,688 B2 | 6/2010 | Oetjen et al. |
| 8,142,876 B2 * | 3/2012 | Ueminami et al. ........... 428/131 |
| 8,575,417 B2 * | 11/2013 | Oetjen et al. .................. 604/367 |
| 2001/0031954 A1 | 10/2001 | Jordan et al. |
| 2002/0007162 A1 | 1/2002 | Cammarota et al. |
| 2002/0062115 A1 | 5/2002 | Wada et al. |
| 2002/0187322 A1 | 12/2002 | Molee |
| 2003/0065299 A1 | 4/2003 | Carlucci et al. |
| 2003/0073966 A1 | 4/2003 | Sosalla et al. |
| 2003/0078553 A1 | 4/2003 | Wada et al. |
| 2003/0082968 A1 | 5/2003 | Sharma et al. |
| 2003/0106825 A1 | 6/2003 | Molina et al. |
| 2003/0109839 A1 | 6/2003 | Costea et al. |
| 2003/0114809 A1 | 6/2003 | Gagliardi et al. |
| 2003/0114811 A1 | 6/2003 | Christon et al. |
| 2003/0114818 A1 | 6/2003 | Benecke et al. |
| 2003/0130632 A1 | 7/2003 | Costea et al. |
| 2003/0158532 A1 | 8/2003 | Magee et al. |
| 2003/0187415 A1 | 10/2003 | Kudo et al. |
| 2004/0015145 A1 | 1/2004 | Miura et al. |
| 2004/0055367 A1 | 3/2004 | Swiecicki et al. |
| 2004/0102748 A1 | 5/2004 | Hirotsu |
| 2004/0122386 A1 | 6/2004 | Mocadlo |
| 2004/0170813 A1 | 9/2004 | Digiacomantonio et al. |
| 2005/0038402 A1 | 2/2005 | Christon et al. |
| 2005/0069574 A1 | 3/2005 | Loughran et al. |
| 2005/0096614 A1 | 5/2005 | Perez et al. |
| 2005/0096618 A1 | 5/2005 | Magee et al. |
| 2005/0124954 A1 | 6/2005 | Adams et al. |
| 2005/0124955 A1 | 6/2005 | Adams et al. |
| 2005/0145523 A1 | 7/2005 | Zander et al. |
| 2005/0148961 A1 | 7/2005 | Sosalla et al. |
| 2005/0148962 A1 | 7/2005 | Warren et al. |
| 2005/0148979 A1 | 7/2005 | Palma et al. |
| 2005/0154365 A1 | 7/2005 | Zander et al. |
| 2005/0165373 A1 | 7/2005 | London Brown |
| 2005/0170726 A1 | 8/2005 | Brunson et al. |
| 2005/0209576 A1 | 9/2005 | Hirotsu |
| 2005/0283129 A1 | 12/2005 | Hammons et al. |
| 2006/0003657 A1 | 1/2006 | Larson et al. |
| 2006/0025739 A1 | 2/2006 | DiPalma et al. |
| 2006/0092431 A1 | 5/2006 | Larson et al. |
| 2006/0111684 A1 | 5/2006 | Berba et al. |
| 2006/0129114 A1 | 6/2006 | Mason et al. |
| 2006/0129116 A1 | 6/2006 | Hughes et al. |
| 2006/0135927 A1 | 6/2006 | Zander et al. |
| 2006/0137568 A1 | 6/2006 | MacDonald et al. |
| 2006/0142710 A1 * | 6/2006 | Kigata et al. .................. 604/361 |
| 2006/0195357 A1 | 8/2006 | Klofta et al. |
| 2007/0003993 A1 | 1/2007 | Kritzman et al. |
| 2007/0016154 A1 | 1/2007 | Christon et al. |
| 2007/0100308 A1 | 5/2007 | Miyairi |
| 2007/0191802 A1 | 8/2007 | Gubernick et al. |
| 2008/0154226 A9 | 6/2008 | Hammons et al. |
| 2008/0208153 A1 | 8/2008 | Oetjen et al. |
| 2008/0255529 A1 | 10/2008 | Christon et al. |
| 2008/0255530 A1 | 10/2008 | Christon et al. |
| 2008/0262454 A1 | 10/2008 | Christon et al. |

FOREIGN PATENT DOCUMENTS

| | | |
|---|---|---|
| EP | 1 208 823 A1 | 5/2002 |
| WO | WO 91/19471 | 12/1991 |
| WO | WO 99/56690 A1 | 11/1999 |
| WO | WO 02/36177 A2 | 5/2002 |

OTHER PUBLICATIONS

EPO Search Report, dated Oct. 31, 2011, 6 pages.

* cited by examiner

PRINTED NONWOVEN WEB AND METHOD FOR MAKING

CROSS REFERENCE TO RELATED APPLICATION

This application is a continuation application of prior U.S. application Ser. No. 11/710,214 filed Feb. 23, 2007 now U.S. Pat. No. 8,142,876.

FIELD OF THE INVENTION

This invention relates to disposable absorbent products, and more specifically to disposable absorbent products having visible images visible on a topsheet thereof.

BACKGROUND OF THE INVENTION

Disposable absorbent articles, such as disposable diapers, sanitary napkins, pantiliners, interlabial devices, incontinent devices, training pants, tampons, and the like, are known in the art. Printing on or below the top surface of an absorbent article is known in the art. Printing to create a signal that masks stains, for example, is known. One currently-marketed disposable absorbent article, ALWAYS® brand sanitary napkins, there is printed on one layer underlying the topsheet a color signal that is visible through the topsheet. By printing on a layer below the topsheet, the color signal can be viewed through the topsheet to provide for a perception of depth within the absorbent article. Depth perception of a printed color signal appears to be particularly effective when utilized with a three-dimensional formed film topsheet, as used on the aforementioned ALWAYS® brand sanitary napkin.

It would be desirable to gain the demonstrated advantages of printing a color signal on a layer below the topsheet of a disposable absorbent article in an alternative manner that either (1) does not require an underlying layer, or (2) can permit elimination of a layer of material, or (3) utilizes less ink or other printed medium to achieve an acceptable level of visual perception by a user.

SUMMARY OF THE INVENTION

A nonwoven web having printed thereon a colorant and/or a composition providing a skin health benefit is disclosed. The nonwoven web can be a three-dimensional, fluid pervious, polymeric web. The nonwoven web can comprise apertures. The apertures are defined in a first surface of the nonwoven web in a first plane of the nonwoven web, and extend in sidewall portions to a second surface in a second plane of the nonwoven web. A colorant or lotion composition can be deposited on at least a portion of the second surface of the nonwoven web.

DETAILED DESCRIPTION OF THE INVENTION

A web, and method and apparatus for making a web are disclosed. The web can be beneficially utilized as a topsheet or other component in a disposable absorbent article. The web can be a nonwoven web or a polymeric film, as each are known in the art for use as topsheets in disposable absorbent articles. In one embodiment, the web can be a nonwoven web that is locally deformed, such as by embossing, to have out-of-plane, i.e., "Z-direction" three-dimensionality. "Z-direction" as used herein has its ordinary meaning as used in the art of nonwoven webs and absorbent articles, and refers to the direction generally orthogonal to the X-Y plane of a generally planar, generally flat web. An embossment or other perturbation made in a generally flat, planar, nonwoven web is considered to be extended in the Z-direction. Z-direction perturbations in a web can be macroscopic, i.e., visible with the unaided eye at a distance of about 12 inches, and as such can effectively increase the bulk of the web. Bulk is a measure that is the inverse of density, i.e., volume per unit mass, and can be increased by increasing the effective thickness of the web without increasing the web's basis weight. The three dimensional protrusions formed by the perturbations can define apertures, and can be uniform in a Z-direction dimensions (i.e, "height") such that the distal ends of the protrusions can be considered to end in a common plane, or surface, as described below with respect to formed films. The web can be a formed film, such as a macroscopically-expanded, three-dimensional, fluid pervious, polymeric web. The description below is in the context of a formed film embodiment, but it is to be understood that in principle, the web, apparatus, and methods disclosed can be adapted to a three-dimensionally formed nonwoven web.

Figure 1:
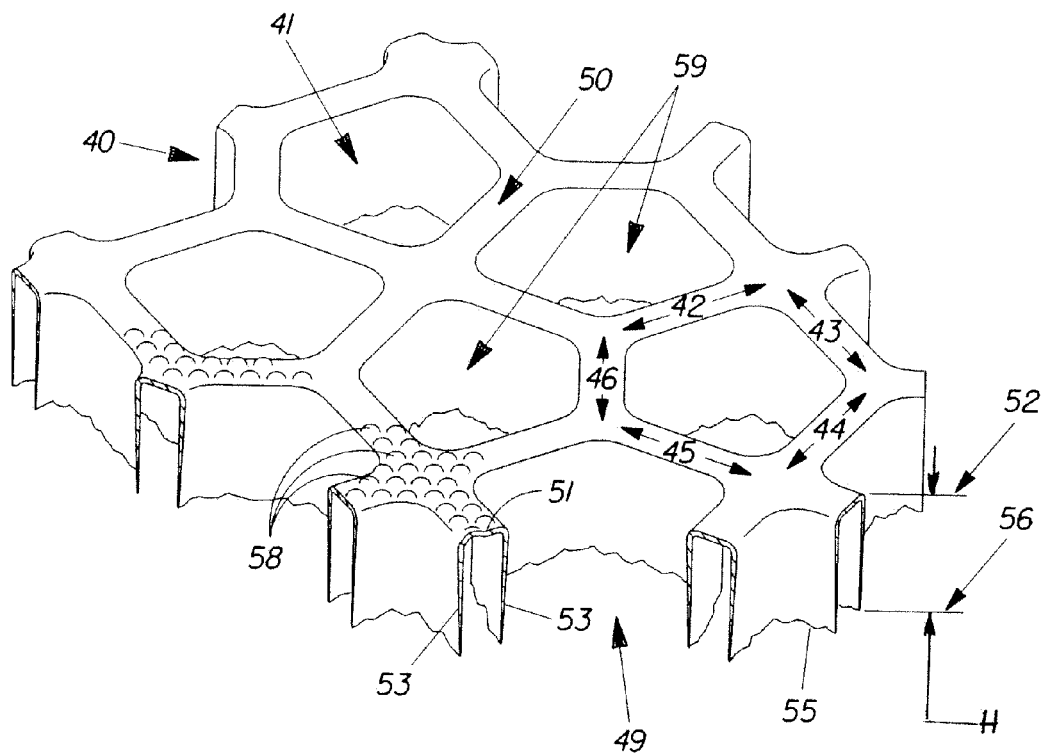
FIG. 1 is a perspective view of a portion of a three-dimensional formed film suitable for use in the present invention.

FIG. 1 is an enlarged, partially segmented perspective illustration of a prior art macroscopically-expanded, three-dimensional, fluid pervious polymeric web 40 formed generally in accordance with U.S. Pat. No. 4,342,314 issued to Radel et al. on Aug. 3, 1982. Webs of this type have been found to be highly suitable for use as a topsheet in absorbent articles such as sanitary napkins, pantiliners, interlabial devices, and the like. The fluid pervious web 40 exhibits a plurality of macroscopic surface aberrations that can be apertures, such as primary apertures 41. Primary apertures 41 are formed by a multiplicity of interconnecting members, such as fiber like elements, e.g., 42, 43, 44, 45 and 46, that are interconnected to one another to define a continuous first surface 50 of the web 40. Each fiber like element has a base portion, e.g., base portion 51, located in plane 52 of first surface 50. Each base portion has a sidewall portion, e.g., sidewall portion 53, attached to each longitudinal edge thereof. The sidewall portions extend generally in the direction of a discontinuous second surface 55 of web 40. The intersecting sidewall portions are interconnected to one another intermediate the first and second surfaces of the web, and terminate substantially concurrently with one another in the plane 56 of the second surface 55. Planes 52 and 56 can be substantially parallel and separated by a distance termed herein as thickness or caliper H. In some embodiments, the base portion 51 may have surface aberrations 58 in accordance with U.S. Pat. No. 4,463,045 issued to Ahr et al. on Jul. 31, 1984.

As used herein, the term "macroscopically expanded" refers to the structure of a web formed from a precursor web or film, e.g., a planar web, that has been caused to conform to the surface of a three-dimensional forming structure so that both sides, or surfaces, of the precursor web are permanently altered due to at least partial conformance of the precursor web to the three-dimensional pattern of the forming structure. The three-dimensional structure results in a first surface (e.g., first surface 50) and a second surface (e.g., second surface 55) that are a predetermined distance apart, the predetermined distance being at least twice, three times, five times, or ten times the thickness of the precursor web or film. Such macroscopically-expanded webs are typically caused to conform to the surface of the forming structure by embossing (i.e., when the forming structure exhibits a pattern comprised primarily of male projections), by debossing (i.e., when the forming structure exhibits a pattern comprised primarily of female depressions, or apertures), or by a combination of both.

As used herein, the term "macroscopic" refers to structural features or elements that are readily visible and distinctly discernable to a human having 20/20 vision when the perpendicular distance between the viewer's eye and the web is about 12 inches. Conversely, the term "microscopic" is utilized to refer to structural features or elements that are not readily visible and distinctly discernable to a human having 20/20 vision when the perpendicular distance between the viewer's eye and the plane of the web is about 12 inches. In general, as used herein, the primary apertures of a web disclosed herein are macroscopic, and surface aberrations, such as hair-like fibrils as disclosed more fully below are considered microscopic.

The term "planar" as used herein to refers to the overall condition of a precursor web or film when viewed by the naked eye on a macroscopic scale, prior to permanently deforming the web into a three-dimensional formed film. In this context, extruded films prior to post-extrusion processing and films that do not exhibit significant degree of permanent macroscopic three-dimensionality, e.g., deformation out of the plane of the film, would generally be described as planar.

As utilized herein, the term "polymeric web" refers to webs comprised substantially completely of polymeric material, such as polymeric films and nonwovens. The term "polymeric film" refers film polymeric webs, including webs made of polyethylene or polypropylene, and commonly used for topsheets and backsheets of disposable absorbent articles. Polymeric films can be made by means well known in the art, including extrusion, cast, blown, and laminate methods such as co-extrusion. The term "nonwoven" or "nonwoven web" refers to nonwoven polymeric webs made of polymeric fibers, such as polyethylene, propylene, PET, and combinations and blends, including bicomponent fibers, split fibers, and staple fibers. Nonwoven webs can be made by means well known in the art, including meltblown, spunlace, carded, airlaid, spunbond, and the like.

As utilized herein, the term "interconnecting members" refers to some or all of the elements of a web, e.g., web 40 in FIG. 1, portions of which serve to define the primary apertures by a continuous network. As can be appreciated from the description of FIG. 1 and the present invention herein, the interconnecting members, e.g., fiber like elements 42, 43, 44, 45, and 46, are structurally continuous, with contiguous interconnecting elements blending into one another in mutually adjoining transition portions. Individual interconnecting members can be best described with reference to FIG. 1 as those portions of the web disposed between any two adjacent primary apertures, originating in the first surface and extending into the second surface. On the first surface of the web the interconnecting members collectively form a continuous network, or pattern, the continuous network of interconnecting members defining the primary apertures, and on the second surface of the web interconnecting sidewalls of the interconnecting members collectively form a discontinuous pattern of secondary apertures.

In a three-dimensional, macroscopically-expanded web, the interconnecting members may be described as channel-like. Their two dimensional cross-section may also be described as "U-shaped", as in the aforementioned Radel '314 patent, or "upwardly concave-shaped", as disclosed in U.S. Pat. No. 5,514,105, issued on May 7, 1996 to Goodman, Jr., et al. "Upwardly-concave-shaped" as used herein, and as represented in FIG. 1, describes the orientation of the channel-like shape of the interconnecting members with relation to the surfaces of the web, with a base portion 51 generally in the first surface 50, and the legs, e.g., sidewall portions 53, of the channel extending from the base portion 51 in the direction of the second surface 55, with the channel opening being substantially in the second surface 55. In general, for a plane cutting through the web, e.g., web 40, orthogonal to the plane, e.g., plane 52, of the first surface 50 and intersecting any two adjacent primary apertures, e.g., apertures 41, the resulting cross-section of an interconnecting member disposed therein will exhibit a generally upwardly concave shape that may be substantially U-shaped.

The term "continuous" when used herein to describe the first surface of a macroscopically-expanded, three-dimensional formed film web, refers to the uninterrupted character of the first surface generally in the plane of the first surface. Thus, any point on the first surface can be reached from any other point on the first surface without substantially leaving the first surface. Conversely, as utilized herein, the term "discontinuous" when used to describe the second surface of a three-dimensionally formed film web refers to the interrupted character of the second surface generally in the plane of the second surface. Thus, any point on the second surface cannot necessarily be reached from any other point on the second surface without substantially leaving the second surface in the plane of the second surface.

Figure 2:
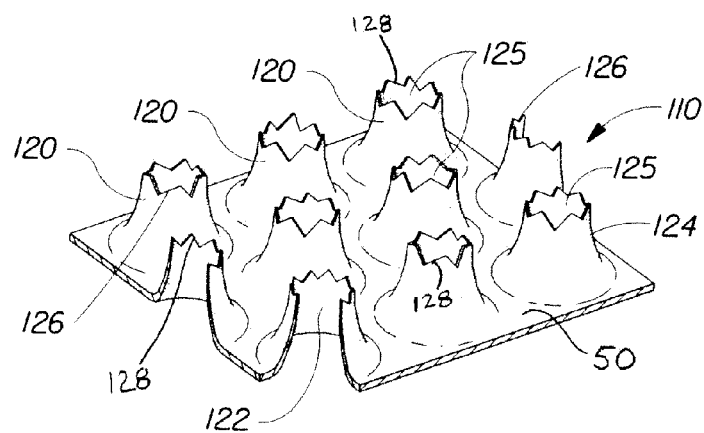
FIG. 2 is a perspective view of a three-dimensional formed film suitable for use in the present invention.

FIG. 2 shows an enlarged, partially segmented, perspective illustration of a portion of another prior art polymeric microapertured web 110 formed generally in accordance with U.S. Pat. No. 4,629,643, issued to Curro et al. The microapertured surface aberrations 120 can be formed by a hydroforming process in which a high-pressure liquid jet is utilized to force the web to conform to a three-dimensional support member. As shown, ruptures which coincide substantially with the maximum amplitude of each micro-apertured surface aberration 120 result in the formation of a volcano-shaped aperture 125 having relatively thin, irregularly shaped petals 126 about its periphery. The relatively thin, petal-shaped edges 128 of the aperture of such a web provide for increased softness impression on the skin of a user when compared, for example, to the web of Ahr '045. It is believed that this softness impression is due to the relative lack of resistance to compression and shear afforded by the surface aberrations having volcano-shaped apertures. For webs of the type depicted in FIG. 2 having both macro-apertures (as shown in the web of FIG. 1) and micro-apertures extending from first surface 50, the caliper H is the dimension from plane 56 of second surface 55 to a plane of a surface corresponding generally to the petal-shaped edges 128 of volcano-shaped apertures 125.

Figure 3:
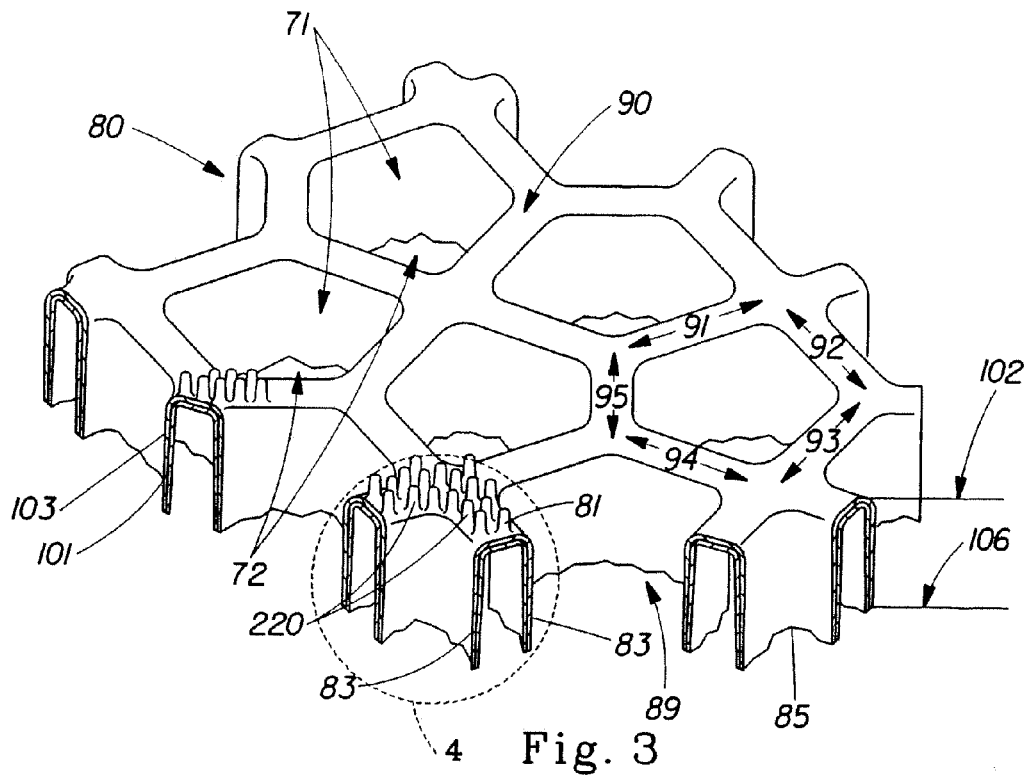
FIG. 3 is a perspective view of a three-dimensional formed film suitable for use in the present invention.

FIG. 3 is an enlarged, partially segmented perspective illustration of a fluid pervious, macroscopically-expanded, three-dimensional polymeric web 80 as taught in U.S. application Ser. No. 10/324,366, filed Dec. 20, 2002, and entitled Polymeric Web Exhibiting a Soft and Silky Tactile Impression. The geometric configuration of the macroscopic surface aberrations, e.g., primary apertures 71, of the polymeric web can be generally similar to that of the web 40 illustrated in FIG. 1. Primary apertures 71 may be referred to as "apertures" or "macro-apertures" herein, and refer to openings in the web that permit fluid communication between a first surface 90 of web 80 and a second surface 85 of web 80. The primary apertures 71 of the web shown in FIG. 3 are defined in the plane 102 of first surface 90 by a continuous network of interconnecting members, e.g., members 91, 92, 93, 94, and 95 interconnected to one another. The shape of primary apertures 71 as projected in the plane of the first surface 90 may be in the shape of polygons, e.g., squares, hexagons, etc., in an ordered or random pattern. In a preferred embodiment primary apertures 71 are in the shape of modified ovals, and in one embodiment primary apertures 71 are in the general shape of a tear drop. Polymer web 80 exhibits a plurality of surface aberrations 220 in the form of hair-like fibrils 225, described more fully below. For webs of the type depicted in FIG. 3 having both macro-apertures 71 and hair-like fibrils 225 extending from first surface 90, the caliper H is the dimension from plane 106 of second surface 85 to a plane of a surface corresponding generally to the distal ends 226 of hair-like fibrils 225.

In a three-dimensional, microapertured polymeric web 80, each interconnecting member comprises a base portion, e.g., base portion 81, located generally in plane 102, and each base portion has sidewall portions, e.g., sidewall portions 83 extending from each longitudinal edge thereof. Sidewall portions 83 extend generally in the direction of the second surface 85 of the web 80 and join to sidewalls of adjoining interconnecting members intermediate the first and second surfaces, 90 and 85, respectively, and terminate substantially concurrently with one another to define secondary apertures, e.g., secondary apertures 72 in the plane 106 of second surface 85.

Figure 4:
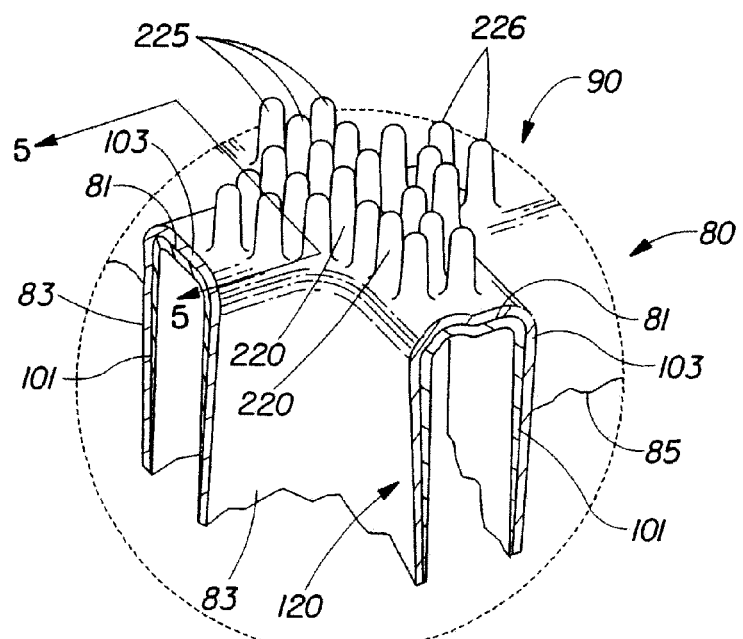
FIG. 4 is an enlarged perspective view of a portion of the three-dimensional formed film shown in FIG. 3.

FIG. 4 is a further enlarged, partial view of the three-dimensional polymeric web 80 shown in FIG. 3. The three-dimensional polymeric web 80 comprises a polymer film 120, i.e., the precursor film, which can be a single layer of extruded polymer or a multilayer co-extruded or laminate film comprising two or more layers. As shown in FIG. 4, film 120 is a two-layer laminate comprising a first layer 101 and a second layer 103. Laminate materials may be co-extruded, as is known in the art for making laminate films, including films comprising skin layers. While it is presently preferred that, as shown in FIG. 4, the polymeric layers, e.g., layers 101 and 103, terminate substantially concurrently in the plane of the second surface 106 it is not presently believed to be essential that they do so. One or more layers may extend further toward the second surface than the other(s).

FIG. 4 shows a plurality of surface aberrations 220 in the form of hair-like fibrils 225. The hair-like fibrils are formed as protruded extensions of the polymeric web 80, generally on the first surface 90 thereof. The number, size, and distribution of hair-like fibrils 225 on polymeric web 80 can be predetermined based on desired skin feel. For applications as a topsheet in disposable absorbent articles, it is preferred that hair-like fibrils 225 protrude only from the base portion 81 in first surface 90 of polymeric web 80, as shown in FIGS. 3 and 4. Therefore, when web 80 is used as a topsheet in a disposable absorbent article, the web can be oriented such that the hair-like fibrils 225 are skin contacting for superior softness impression, and yet, the hair-like fibrils 225 do not obstruct fluid flow through macro-apertures 71. Moreover, having hair-like fibrils 225 with closed distal portions 226 results in reduced rewet, i.e., reduced amounts of fluid being re-introduced to the surface of the topsheet after having been first passed through the topsheet to underlying absorbent layers.

Figure 5:
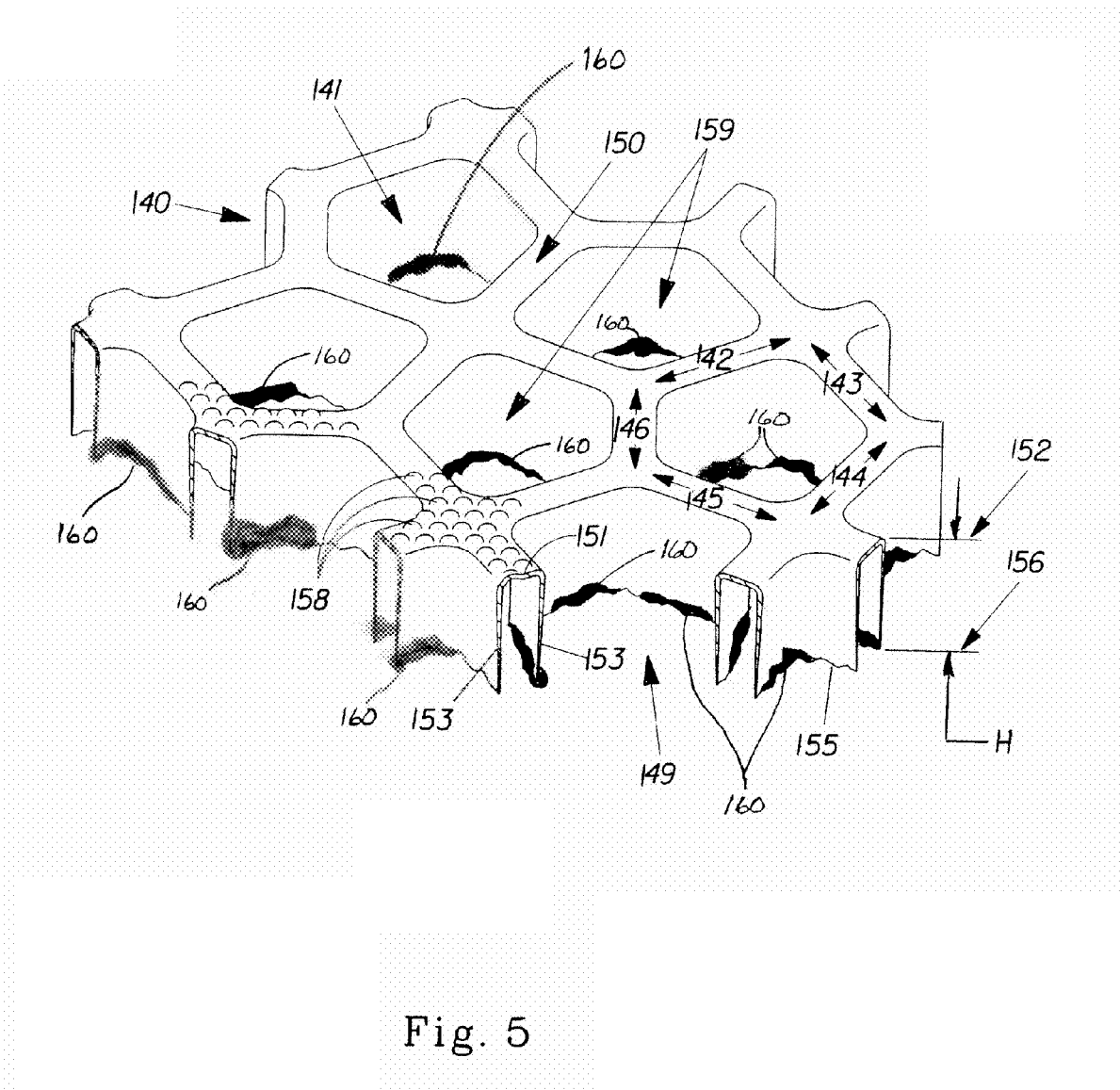
FIG. 5 is a perspective view of a three-dimensional formed film of the present invention.

FIG. 5 shows a web of the present invention, the web 140 being in this embodiment in all respects like the web of FIG. 1 but having printed on the second surface 155 thereof a colorant, the colorant in this embodiment being present in the form of ink deposits 160. Ink deposits 160 can be described as discrete, spaced apart deposits of ink Colorant can be any of colorants suitable for deposition onto a polymeric film, including water-based inks and dyes, solvent-based inks and dyes, UV-curable inks or dyes, paint, pigment, or liquid colorants such as food coloring. Colorant can be produce a color contrasting with the color of the web 140 and can be primary colors and common colors such as red, green, blue, yellow, pink, purple, orange, or black. If web 140 is dark colored, colorant can be light colors such as light gray, silver, white, or beige. The fluid pervious web 140 exhibits a plurality of macroscopic surface aberrations that can be apertures, such as primary apertures 141. Primary apertures 141 are formed by a multiplicity of interconnecting members, such as fiber like elements, e.g., 142, 143, 144, 145 and 146, that are interconnected to one another to define a continuous first surface 150 of the web 140. Each fiber like element has a base portion, e.g., base portion 151, located in plane 152 of first surface 150. Each base portion has a sidewall portion, e.g., sidewall portion 153, attached to each longitudinal edge thereof. The sidewall portions extend generally in the direction of a discontinuous second surface 155 of web 140. The intersecting sidewall portions are interconnected to one another intermediate the first and second surfaces of the web, and terminate substantially concurrently with one another in the plane 156 of the second surface 155. Planes 152 and 156 can be substantially parallel and separated by a distance termed herein as thickness or caliper H. In general, caliper H of webs of the present invention useful as topsheets on disposable absorbent articles can be in the range of 0.1 to 2 millimeters, and can range in 0.01 mm increments between these values. Caliper H can be from 0.40 to 0.60 millimeters. Caliper H can average about 0.44 millimeters. In some embodiments, the base portion 151 may have surface aberrations 158 in accordance with U.S. Pat. No. 4,463,045 issued to Ahr et al. on Jul. 31, 1984.

In some embodiments, sidewall portions 153 end substantially uniformly such that the second surface 155 coincides substantially completely with plane 156. However, in some embodiments, sidewall portions 153 can end in substantially non-uniformly, such as in a somewhat jagged pattern wherein various portions have differing height H dimensions. In such an embodiment, plane 156 can be considered located at an average distance H determined by second surface 155. In each embodiment, sidewall portions are considered to extend to a second surface in a second plane of the web.

Ink deposits 160 are shown in FIG. 5 as being predominantly at the distal ends of sidewalls 153, i.e., substantially only on the second surface 155. Because sidewalls can be relatively thin, including being thinned from the original thickness of the starting film web material due to the process of making, and because ink can be deposited in droplets having dimensions greater than the sidewall thickness, in some embodiments ink deposits can extend some distance on the sidewall 153 away form the distal end, and yet still be considered substantially only on the second surface 155. Therefore, in one embodiment, colorants in the form of ink deposits 160 on the second surface 155 can be on the film edge, or primarily on the film edge at the distal ends of sidewall portions 153. In other embodiments, in addition to being on the film edge at the distal ends of sidewall portions 153, ink can be on other parts of the sidewall portions 153, including on the inner or outer surfaces of sidewall portions 153.

One advantage to having colorant deposited on at least a portion of the second surface of a three-dimensional, formed film web, such as a web illustrated in FIG. 5, is the impression of depth that is created. When used as a topsheet on an absorbent article, a web having colorant deposited at a plane below the top surface provides for a visual impression of depth and richness that is pleasing to consumers. In addition, because the colorant is actually placed at a plane below the top surface, the colorant is, in fact, as far away from the user's skin when the web is used as a topsheet on an absorbent article. This remote placement can be beneficial for certain colorants in which it is undesirable for the colorant to be on or near the top surface of the topsheet.

One advantage to the web of the present invention, and the methods for making as described below, is that colorant, or a combination of colorants can be applied to the web at differing areas of sidewall portions 153. For example, a colorant can be applied to be limited to being at substantially second surface 155. Or the colorant, or another colorant having a different color, can be applied midway between first surface 150 and second surface 153. If more than one color of colorant is used, multiple planes of color can be created to provide novel visual effects to a user viewing the web from the first surface side. When used as a topsheet in an absorbent article, various colorants, colors of colorants, and placement options can be combined to create novel visual shapes, depth effects, color combinations. By way of example, in one embodiment, a first colorant can be applied to the second surface of a central region of a topsheet for a sanitary napkin, and a second colorant having a different color can be applied to the second surface of a side or end region of the topsheet. In another embodiment, a first colorant can be applied to the second surface of a central region of a topsheet for a sanitary napkin in a swirl shape, and a second colorant having a different color can be applied to the mid-sidewall portions in the same region of the topsheet, and in the same swirl pattern to provide for an optical effect. Of course, any combination of colorant, color, deposition location, shape of deposition can be contemplated, each having its own novel visual effect.

Ink deposits 160 on the second surface 155 of web 140 can be applied by a printing process, such as gravure printing and flexographic printing as described below. Other printing processes as are known in the art can be used, each with various advantages and disadvantages. The advantage of printing via a flexographic printing process is that the nip setting at the printing stage can be adjusted and set such that only the second surface 155 of web 140 contacts the inked roll in a highly controllable manner. The result is that ink deposits 160 can be precisely controlled so as to be applied on a surface of web 140 spaced a predetermined distance from first surface 150. As discussed above, when web 140 is used as a topsheet on a disposable absorbent article, ink deposits 160 on the second surface 155 can render a perception of depth visible from the user-facing side of the disposable absorbent garment. By achieving a perception of depth in this manner, underlying layers such as secondary topsheets having printed signals can be eliminated without loss of the color signal capability. Also, by printing only on the second surface 155 of a formed film, the amount of ink utilized for a commercially viable visual signal can be significantly reduced, as compared to printing a color signal on an underlying layer, such as a secondary topsheet or core layer.

Ink deposits 160 can be closely spaced so as to form a substantially complete coverage of second surface 155, or they can be spaced relatively far apart. The ink deposits 160 can be limited to substantially only on the very ends of sidewall portions 153, or the ink deposit 160 can extend a substantial distance up sidewall portion 153 in the direction of first surface 150. In one embodiment ink deposits 160 are colorfast so that they do not dissolve, degrade, or run when insulted with at least one of water, urine, or menses. In another embodiment, ink deposits 160 can be soluble in at least one of water, urine, or menses, such that upon liquid insult the imprinted color changes or disappears. Such color change can indicate wetness, volume of fluid, position of fluid, and/or type of fluid.

Figure 6:
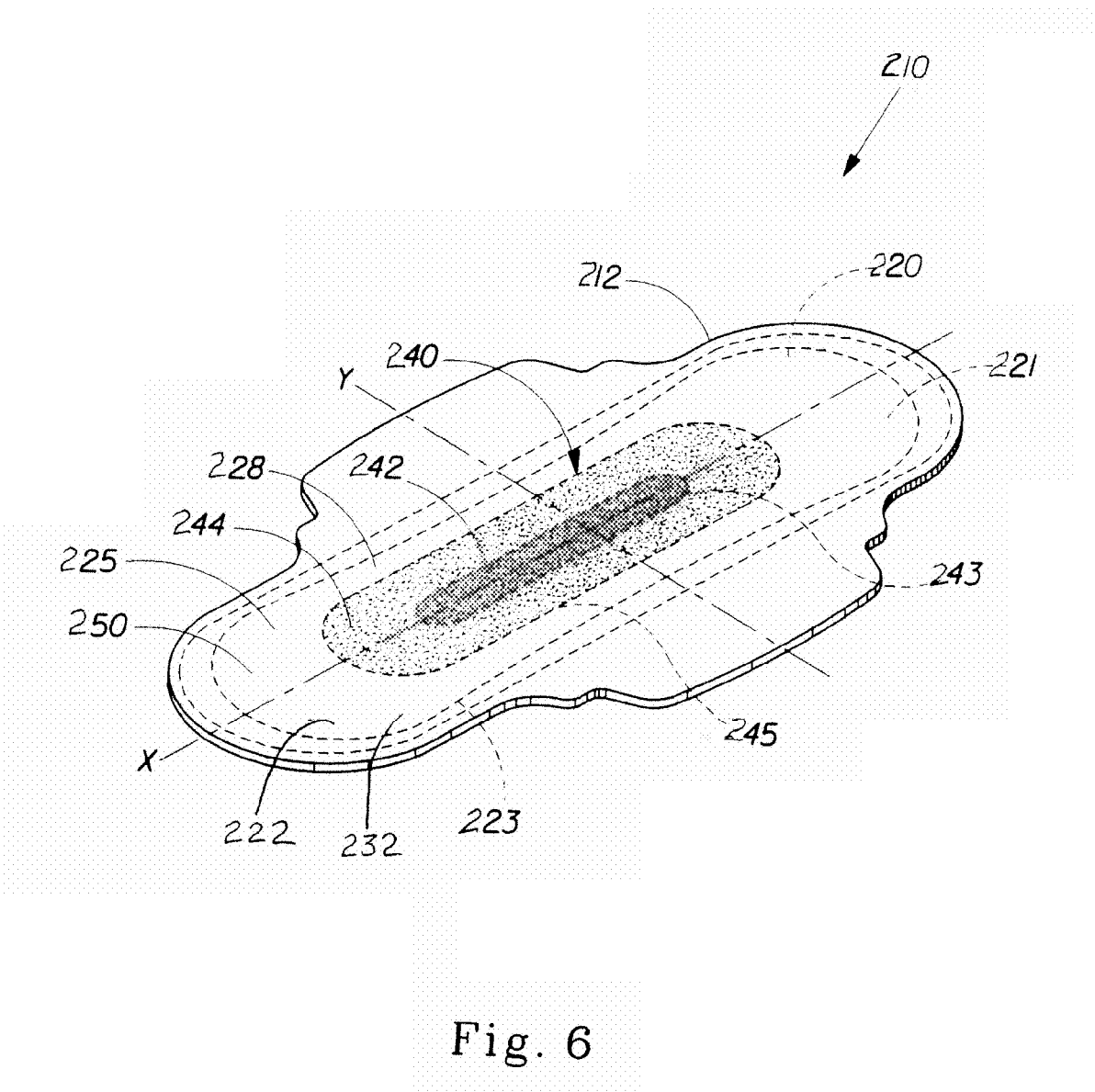
FIG. 6 is a perspective view of a disposable absorbent article of the present invention.

In one embodiment, ink deposits 160 can be printed so as to make a graphic image visible from the body-facing side of a disposable absorbent article. For example, as shown in FIG. 6, the image can be similar to that taught in co-pending, co-owned U.S. patent application Ser. No. 10/025,059, filed Dec. 19, 2001, entitled Absorbent Article, or co-pending, co-owned U.S. patent application Ser. No. 10/967,454, filed Oct. 18, 2004, entitled Absorbent Article.

FIG. 6 provides a perspective view of the absorbent article 210. The absorbent article 210 herein has an upper surface 222, a lower surface (not seen), and a periphery 212 comprising a topsheet 225 having a bottom surface (not shown) and a viewing surface 232 positioned opposite to the bottom surface. The viewing surface 232 faces upwardly towards the upper surface 222 of the absorbent article 210. The absorbent article 210 further comprises a backsheet 223 having a garment facing surface (not shown) and a user facing surface positioned oppositely to the garment facing surface, the backsheet 223 being joined to the topsheet 225, as is common and known in the art. The absorbent article 210 also comprises an absorbent core 220 having a top surface 221 and a bottom surface (not shown) that is positioned opposite to the top surface 221. The absorbent core 220 is positioned between the topsheet 225 and the backsheet 223, as is common and known in the art.

The ink deposits 160 can render visible from the viewing surface 232 a graphic, such as graphic 240 shown in FIG. 6. In the embodiment shown in FIG. 6 the absorbent article 210 has at least two portions, i.e., a portion comprising graphic 240 and a portion 250 which does not comprise a graphic 240. The graphic 240 and the non-graphic portion 250 can be viewable from the viewing surface 232 of the topsheet 225. The graphic 240 can have at least two shades, a first shade 242 and a second shade 244. In one embodiment, as is shown in FIG. 6, the first shade 242 can be positioned substantially within the second shade 244. The second shade 244 can be different, either in lightness, darkness, and/or color, from the first shade 242. The multi-shades can operate to create an additional perception of depth within the absorbent article by a user looking upon the viewing surface 22 of the topsheet 225.

While the graphic shown in FIG. 6 is similar to the graphic shown in the aforementioned U.S. patent application Ser. No. 10/025,059, in the present invention the shape, size, coloration, placement, and intensity of graphic 240 can be varied in ways limited only by the size of the substrate and the printing techniques employed. For example, by use of letter press, lithographic, screen printing, flexographic or gravure printing techniques, virtually any graphic in any color or color combination can be rendered on topsheet 225. Moreover, by adjusting processing variables such as the nip between rollers in a flexographic process, the amount of ink and the position of ink can be varied to give various impressions of color intensity, brightness/darkness, hue, saturation, and depth perception.

Figure 7:
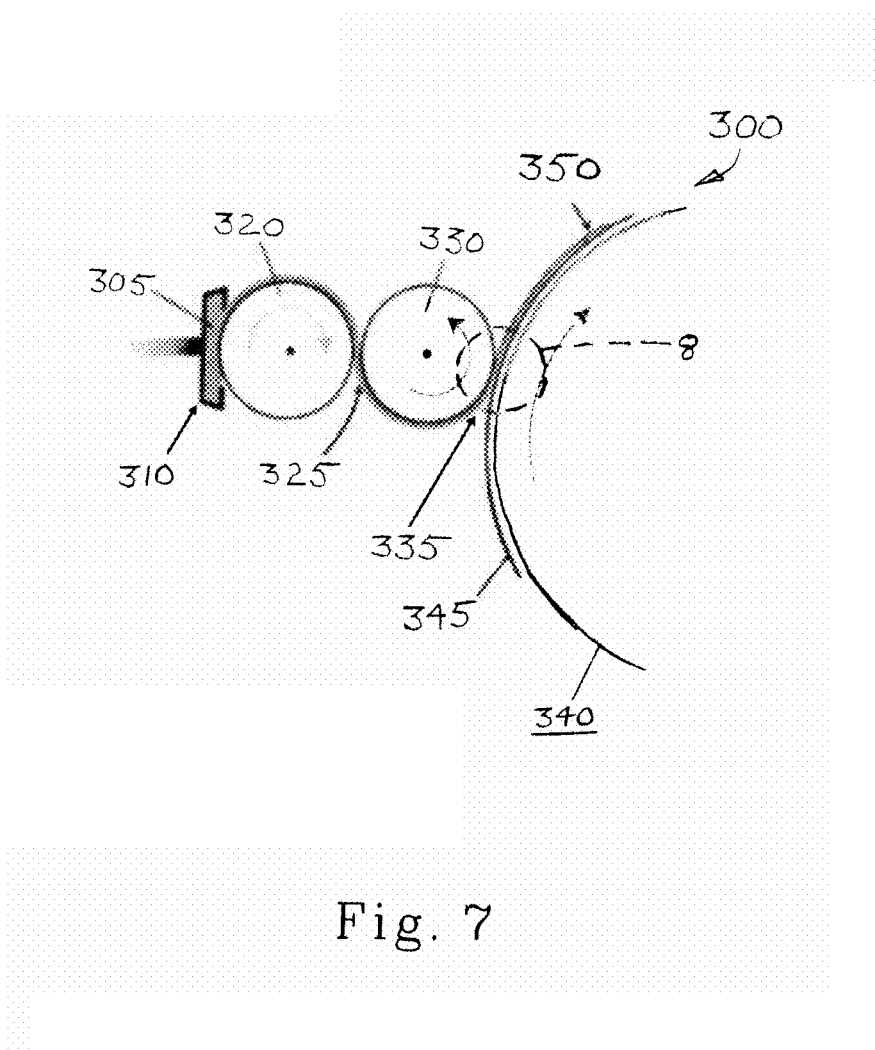
FIG. 7 is a schematic representation of a flexographic printing process of the present invention.

In one embodiment, graphic 240 or other printed image can be imparted to a web, such as topsheet 225 by means of a flexographic printing process, such as that shown schematically in FIG. 7. Flexographic printing process 300 can utilize any of known flexographic printing apparatus and equipment, including processing means known in the art. As shown, ink 305 is supplied in a chamber 310 comprising a doctor blade as is known in the art, and which is in operative relationship with an anilox roller 320 to which ink from the chamber 310 is transferred in a uniform manner as the anilox roller 320 rotates in the direction indicated. Anilox roller 320 is in operative relationship with a plate roller 330 such that at transfer nip 340 ink is transferred from the anilox roller 320 to the plate roller 330. The plate roller 330 picks up ink from the anilox roller 320 in a pattern corresponding to the pattern desired to be printed on a substrate 345. The substrate 345 on which the pattern will be printed, such as a web for a topsheet of a disposable absorbent article, such as the sanitary napkin of FIG. 6, is fed onto the central impression drum 340 (in any conventional manner, not shown), which is rotating in the direction shown in FIG. 7.

As substrate 345 enters the printing nip 335 formed by the operational relationship of the surfaces of the plate roller 330 and the central impression roller 340, the ink 305 on the surface of the plate roller 330 makes contact with, and is transferred to, the substrate 345. Sometimes referred to as an ink impression, the ink transfer pattern corresponds to the graphic 240 that is then visible on printed web 350 and will ultimately be visible from the viewing surface 232 of the topsheet 225 of an absorbent article.

Alternatives to the described flexographic printing process can be implemented. For example, a plurality of printing nips 335 can be arranged, each with its corresponding ink supply and anilox/plate rollers such that multiple patterns and graphics in multiple colors and color intensities can be imparted to substrate 345. In one embodiment, two such printing nips 335 can be used, each nip delivering color in a registered pattern to render a two-color graphic image to substrate 345, which image can then be registered so as to be appropriately disposed on the viewing surface 232 of the topsheet 225 of an absorbent article. In some embodiments, when multiple print operations are performed, it can be necessary that the ink from one printing operation dry sufficiently before the next printing operation. Therefore, in one embodiment, between printing operations there can be operatively positioned drying means, such as infra-red heating, UV light curing, forced air drying, and the like, as is known in the art.

Figure 8:
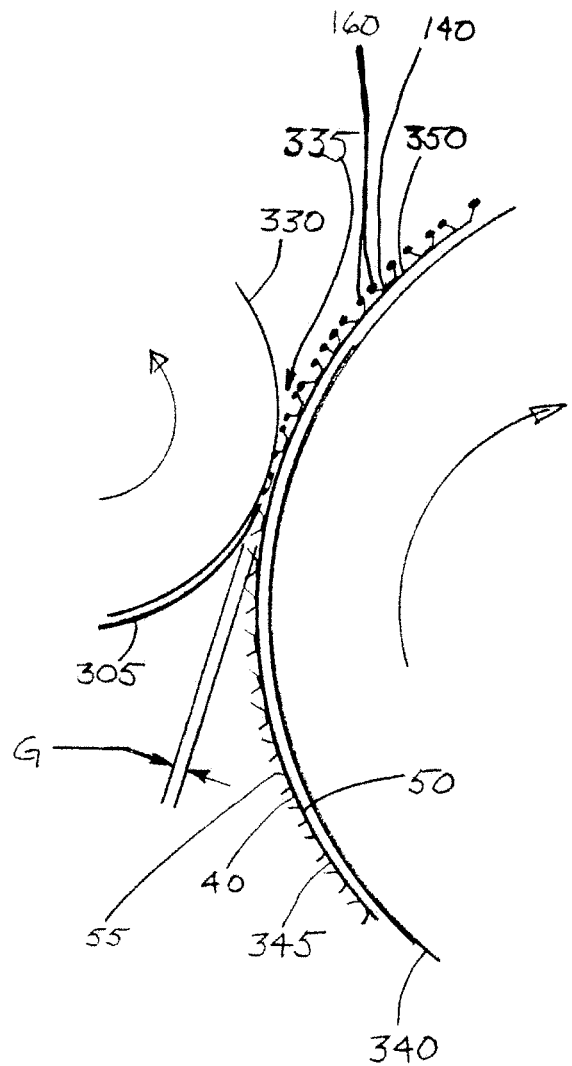
FIG. 8 is a detail of the printing process shown in FIG. 7.

There are many advantages to printing images on three-dimensional, formed film webs by means of the present invention. For example, as shown in FIG. 8, a web, such as web 40 shown in FIG. 1 can be printed in a flexographic printing process with the first surface 50 facing into or on the central impression drum 340 and second surface 55 facing outwardly with respect to the central impression drum 340. The gap G between plate roller 330 and the central impression roller 340 can be set such that ink transfers only to the second surface 55 of web 40 that, in this embodiment, is the substrate 345 that gets printed to be the printed web 350. Once printed, the printed web 350 is a web 140 of the present invention as depicted in FIG. 5. Ink has been transferred via the flexographic process to be deposited only on the second surface 155 and, depending on the gap G, on portions of side walls 153.

Figure 9:
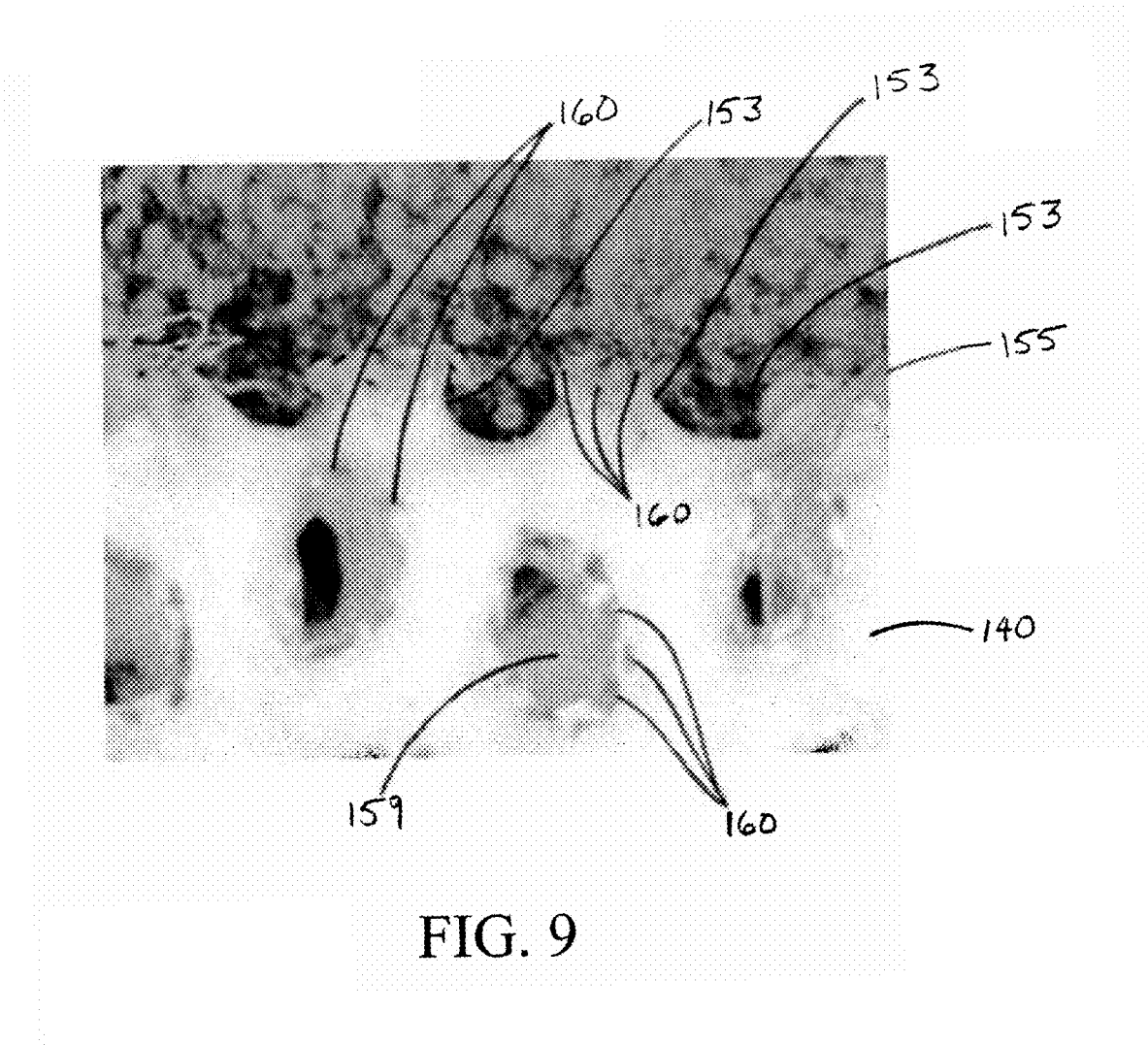
FIG. 9 is a photomicrograph of a web of the present invention.

Gap G can be adjusted depending on the caliper H of the three-dimensional, formed film webs substrate 345. In one embodiment, gap G can be substantially equal to caliper H such that only the very ends of sidewall portions 153 in second surface 155 have ink deposited thereon. In another embodiment, gap G can be less than caliper H such that sidewall portions 153 are compressed through printing nip 335, resulting in ink being deposited on a portion of the sidewalls 153. FIG. 9 is a photomicrograph showing about a 3 mm long (horizontally in FIG. 9) section of the second surface 155 of a web 140 of the present invention showing ink deposits 160 on the ends of sidewall portions 153 at substantially the second surface 155. FIG. 9 shows the underside of a web similar to that shown in FIG. 5, the "underside" being used to denote the side of the web opposite first surface 150, and including the second surface 155. In actual use the either side could be the "underside" so the term is used here simply to denote the side printed, which happens to be the underside as oriented in FIG. 5, for example. As configured in FIG. 9, web 140 is folded so as to better show at the top of the FIG., the cone-like structure formed by the sidewall portions 153. As shown, the ink 305 is printed in a pattern of closely spaced dots on the distal ends of the sidewall portions 153 by a flexographic printing process as described above with respect to FIG. 7. For the three-dimensional, formed film webs substrate 345 printed and depicted in FIG. 9 as web 140, the ink is a water based ink available as GCOF7835747 RD 11 from Sun Chemical, applied to a three-dimensional, formed film made by Tredegar Film Products, Haung Pu plant in Guangzhou, GD, China, having a caliper H of 0.44 mm (when measured under load of 14.7 g/sq cm), in a flexographic PROGLIDE® printing process, made by Mark Andy/Comco, Inc. 910 Lila Ave., Milford, Ohio, in which gap G was adjusted to be about 0.01" (0.254 mm).

Figure 10:
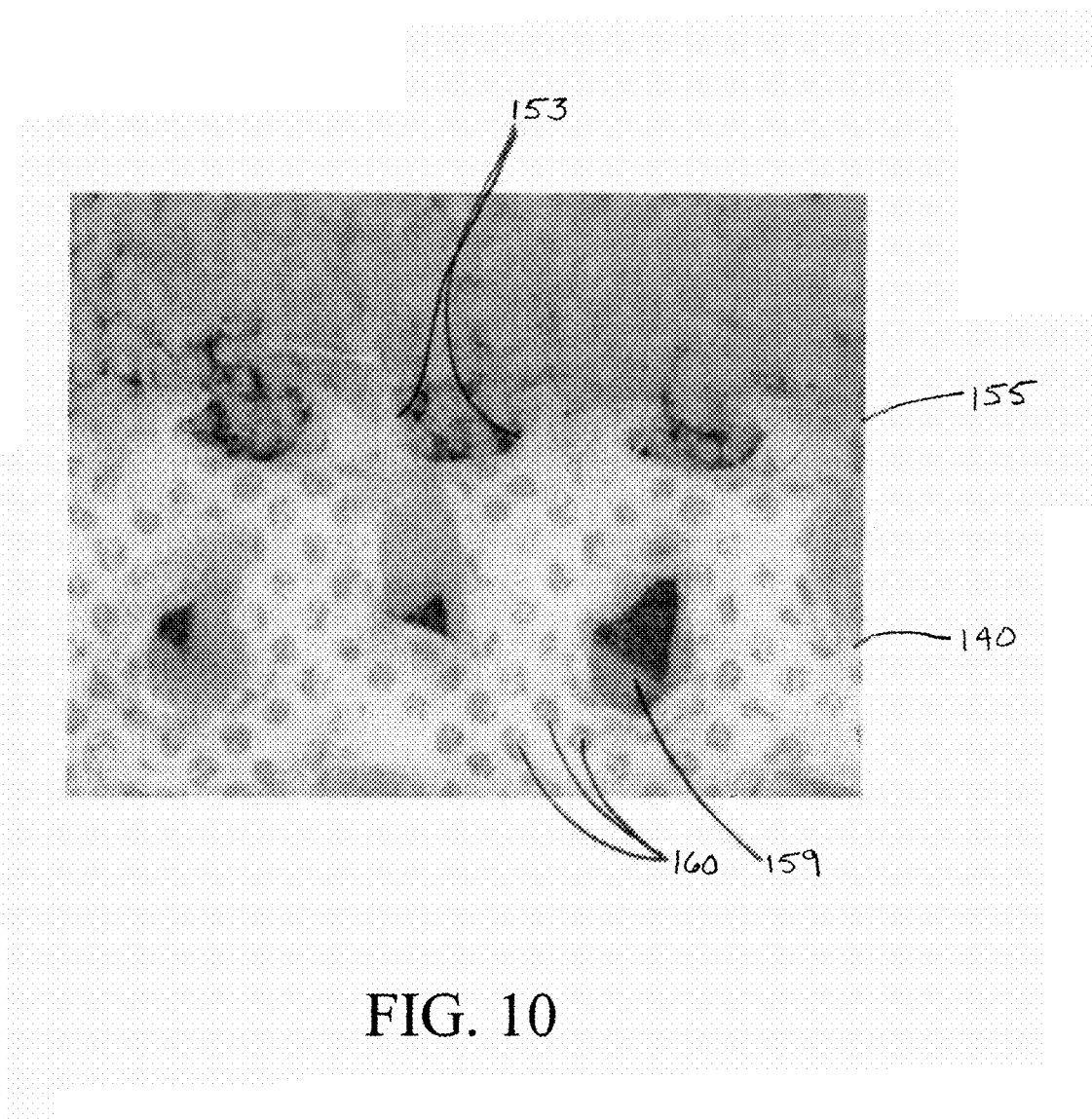
FIG. 10 is a photomicrograph of a web of the present invention.

In another embodiment, gap G can be adjusted such that at printing nip 335 three-dimensional, formed film webs substrate 345 is significantly compressed such that ink is deposited on the virtually all surfaces of printed web 140 except the first surface, such as first surface 50 of the web shown in FIG. 1. FIG. 10 is a photomicrograph showing about a 3 mm long (horizontally in FIG. 10) section of the second surface 155 of a web of the present invention showing ink deposited on virtually the entire underside of web 140, the term "underside" being used to denote the side of the web opposite first surface 150, and including the second surface 155. In actual use the either side could be the "underside" so the term is used here simply to denote the side printed, which happens to be the underside as oriented in FIG. 5, for example. As configured in FIG. 10, web 140 is folded so as to better show at the top of the FIG. the cone-like structure formed by the sidewall portions 153. As shown in FIG. 10, the cone-like structures have been somewhat deformed by compression in the printing process, and the ink 305 is printed in a pattern of closely spaced dots over virtually the entire underside of the web by a flexographic printing process as described above with respect to FIG. 7. For the three-dimensional, formed film webs substrate 345 printed and depicted in FIG. 10, the ink is a solvent based ink available as CROFS7711705 DPO-149 made by Sun Chemical, applied to a three-dimensional, formed film made by Tredegar Film Products, Haung Pu plant in Guangzhou, GD, China having a caliper H of 0.44 mm (when measured under load of 14.7 g/sq cm) in a flexographic PROGLIDE® printing process made by Mark Andy/Comco, Inc. 910 Lila Ave., Milford, Ohio in which gap G was adjusted to be about 0.0" (0.0 mm).

Figure 11:
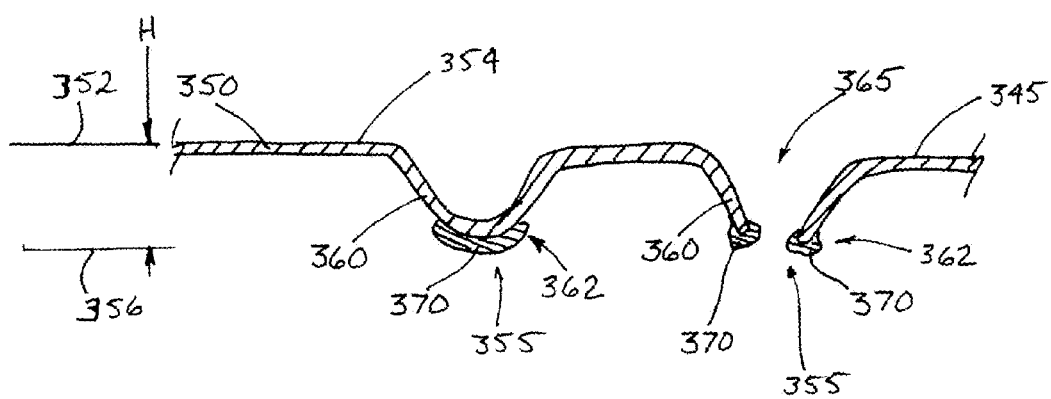
FIG. 11 is a schematic cross section of a nonwoven web of the present invention.

In one embodiment the web of the present invention can be described as a three-dimensional, fluid pervious, web comprising a pattern of protrusions. As shown in FIG. 11, the substrate 345 can comprise a nonwoven web 350 made by known processes including meltblown, spunbond, carding, airlaid, and wetlaid (e.g., paper), and the fibers can be synthetic, bicomponent, cellulosic, nanofibers, microfibers, shaped fibers, surfactant treated fibers, and other fiber types as known in the art, and the web can have sufficient light transmittance such that a printed signal on one side can be seen through the web to the other side. Protrusions 360 can be produced by means known in the art, including hot-pin punching, hot-pin aperturing, embossing, hydroforming, and vacuum forming Two protrusions 360 are shown in the partial cross sectional view of FIG. 11, one having a closed distal end and one having an open, apertured distal end. Protrusions 360 can extend in sidewall portions to distal ends 362 that collectively define a discontinuous second surface 355 in a second plane 356 of the web. Colorant 370, such as ink or dye, can be deposited on at least a portion of the distal ends 362 of protrusions 360, i.e., on the second surface 355 of the web. Protrusions 360 can include or define apertures 365, the apertures being defined in a first surface 354 of said web in a first plane 352 of the web, and extending in sidewall portions to apertures substantially in the second plane thereof. The distance H, which can be considered as the effective thickness of the three-dimensional web 350, between the first plane 352 and the second plane 356 can be twice the average thickness of the base nonwoven web, or three times, or four times, or at least about five times. A web of this type can be beneficially used in sanitary napkins because a topsheet utilizing such a web does not require an underlying layer to provide a color signal visible to a user from the topsheet surface. Further, by printing on a nonwoven web utilized as a topsheet, the manufacturer can eliminate a layer of material such as a secondary topsheet if the secondary topsheet was otherwise utilized as a printing surface on which to print a color signal visible to a user from the topsheet surface. Further, printing a color signal on the nonwoven web utilized as a topsheet as described herein utilizes less ink or other printed medium to achieve an acceptable level of visual perception by a user. By printing ink, for example, only on the distal portions of, i.e., the tips, of the protrusions of the second surface, a relatively lesser amount of ink can suffice to provide a commercially-acceptable visual signal to a user of a disposable absorbent product.

In one embodiment, therefore, the web of the present invention can be described as a three-dimensional, fluid pervious, polymeric web, the web comprising a pattern of interconnecting members, the interconnecting members defining apertures, the apertures being defined in a first surface of said web in a first plane of said web, and extending in sidewall portions to a second surface in a second plane of the web, and wherein ink is deposited on at least a portion of the second surface of the web. A web of this type, sometimes referred to as a macroscopically-expanded formed film, has beneficial use in sanitary napkins, because a topsheet utilizing such a web does not require an underlying layer to provide a color signal visible to a user from the topsheet surface. Further, by printing on a web utilized as a topsheet, the manufacturer can eliminate a layer of material such as a secondary topsheet if the secondary topsheet was otherwise utilized as a printing surface on which to print a color signal visible to a user from the topsheet surface. Further, printing a color signal on the web utilized as a topsheet as described herein utilizes less ink or other printed medium to achieve an acceptable level of visual perception by a user. By printing ink, for example, only on the tips of the macroscopically-expanded cones of the second surface, a relatively lesser amount of ink can suffice to provide a commercially-acceptable visual signal to a user of a disposable absorbent product.

In another embodiment, lotions, surfactants, creams, and other compositions providing skin health benefits can be applied to the second surface of a web, wherein the description above applies, with, for example, lotion substituted for a colorant such as ink or dye. In one embodiment, for example, a clear or color-tinted lotion of petrolatum can be applied by known processes, such as by sufficiently heating for application by flexo-graphic printing means. Once deposited on the web, the heated petrolatum composition can then be cooled to solidify in place, such as on sidewall portions of the web. In this manner, lotions and lotion compositions can be applied alone, or as the colorant, or with a colorant, or in combination with multiple colorants in multiple locations on the web of the present invention, to provide for skin health benefits. Lotions compositions, for example, can be applied to the second surface of a web utilized as a topsheet, such that during use, due to body heat, wearing motion, or fluid migration, the lotion composition can come into contact with the wearer's skin.

In another embodiment, a nonwoven/formed film laminate can be printed. In one embodiment, a nonwoven web can be joined, such as by adhesive or by thermal bonding to a surface of a formed film, either before or after forming into a three-dimensional, fluid pervious, polymeric web. In this manner, a formed film having a soft, fibrous surface can be achieved.

In another embodiment, webs having tufts formed therein, including laminates of films and nonwovens, can be printed as disclosed herein. In one embodiment, the tufts can be formed by needle punching, or by the rotary methods known as SELF'ing, rotary knife aperturing, and the like, as disclosed in co-pending, commonly assigned U.S. Ser. No. 11/156,020, filed 17 Jun. 2005; Ser. No. 10/737,306, filed 16 Dec. 2003; Ser. No. 10/737,430, filed 16 Dec. 2003. The method of the present invention can be utilized to deposit a lotion, colorant, or other fluid material on the tips of tufts. In one embodiment, the method of the present invention can be used to print inks or dyes only on the tips of tufts of a tufted nonwoven or laminate web.

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A three-dimensional, fluid pervious, nonwoven web, said web comprising a first surface and a second surface opposite the first surface, the web further comprising a pattern of protrusions extending in sidewall portions to distal ends, wherein said protrusions have an inner surface and an outer surface, wherein said inner surface comprises the first surface and wherein said outer surface comprises the second surface, wherein a colorant is deposited on said web, said colorant being deposited substantially only on said distal ends of said protrusions and wherein said colorant is deposited at least in part on the outer surface.

2. The web of claim 1, wherein said colorant is selected from the group consisting of inks, dyes, and pigments.

3. The web of claim 1, wherein said colorant is selected from the group consisting of water-based inks and solvent-based inks.

4. The web of claim 1, wherein said colorant is present as discrete, spaced apart deposits of ink.

5. The web of claim 1, wherein said colorant is deposited on at least a portion of said sidewall portions.

6. The web of claim 1, wherein said web has a light transmittance such that said colorant can be seen through said web.

7. The web of claim 1, wherein said protrusions comprise apertures.

8. A disposable absorbent article comprising a topsheet, said topsheet comprising a three-dimensional, fluid pervious, nonwoven web, said web comprising a first surface and a second surface opposite the first surface and a pattern of protrusions extending in sidewall portions to distal ends, wherein said protrusions have an inner surface comprising the first surface and an outer surface comprising the second surface, wherein a colorant is deposited on said web, said colorant being deposited substantially only on said distal ends of said protrusions, and wherein said colorant is deposited at least, in part, on the outer surface.

9. The disposable absorbent article of claim 8, wherein said article is selected from the group consisting of a disposable diaper, a urinary incontinence device, a sanitary napkin, and a pantiliner.

10. The disposable absorbent article of claim 8, wherein said article is a sanitary napkin, and said colorant is applied by printing on said second surface.

11. The disposable absorbent article of claim 8, wherein said colorant is deposited substantially on said second surface and said sidewall portions.

12. A three-dimensional, fluid pervious, nonwoven web, said web comprising a first surface and a second surface opposite the first surface and a pattern of protrusions extending in sidewall portions to distal ends, said protrusions having an inner surface comprising the first surface and an outer surface comprising the second surface, and wherein a composition providing a skin health benefit is deposited on said web, said composition being deposited substantially only on said second surface of said web.

13. The web of claim 12, wherein said composition is selected from the group consisting of, lotions, surfactants, and creams.

14. The web of claim 12, wherein said composition comprises petrolatum.

15. The web of claim 12, wherein said composition is present as discrete, spaced apart deposits of ink.

16. The web of claim 12, wherein said composition is deposited on at least a portion of said sidewall portions.

17. The web of claim 12, wherein said web has a caliper measured between said first plane and said second plane of from about 0.1 mm to 2 mm.

18. The web of claim 12, wherein said web is a topsheet on a disposable absorbent article.

19. The web of claim 18, wherein said disposable absorbent article is selected from the group consisting of a disposable diaper, a urinary incontinence device, a sanitary napkin, and a pantiliner.

20. The web of claim 12, wherein said nonwoven web is combined as a laminate with a polymeric film web.

* * * * *